United States Patent [19]

Dziabo et al.

[11] Patent Number: 5,279,673
[45] Date of Patent: Jan. 18, 1994

[54] METHODS TO DISINFECT CONTACT LENSES

[75] Inventors: Anthony J. Dziabo, El Toro; Hampar Karageozian, Laguna Hills; Paul S. Ripley, Irvine, all of Calif.

[73] Assignee: Allergan, Inc., Irvine, Calif.

[21] Appl. No.: 461,405

[22] Filed: Jan. 5, 1990

[51] Int. Cl.$^5$ .......................... B08B 3/04; B08B 3/08
[52] U.S. Cl. ........................................ 134/26; 134/27; 134/28; 134/42; 252/95; 252/174.23; 252/100; 424/661; 424/468; 514/839; 514/840
[58] Field of Search .............. 134/42, 26, 27, 28; 252/95, 174.23, 100; 424/661, 468; 514/839, 840

[56] References Cited

U.S. PATENT DOCUMENTS

| | | |
|---|---|---|
| Re. 23,218 | 4/1950 | Levy et al. .................... 8/105 |
| Re. 32,672 | 5/1988 | Huth et al. .................... 252/95 |
| 2,436,134 | 1/1948 | Aston ............................ 23/152 |
| 3,123,521 | 3/1964 | Wentworth .................... 424/661 |
| 3,278,447 | 10/1966 | McNicholas ................. 252/187 |
| 3,591,515 | 7/1971 | Lovely ........................ 424/661 |
| 3,910,296 | 10/1975 | Karageozian et al. ........... 134/2 |
| 3,912,451 | 10/1975 | Gaglia, Jr. .................... 134/42 |
| 4,011,941 | 3/1977 | Parsons ........................ 206/5.1 |
| 4,084,747 | 4/1978 | Alliger ..................... 252/187.23 |
| 4,084,747 | 3/1978 | Alliger ..................... 252/187 R |
| 4,104,190 | 8/1978 | Hartshorn .................... 252/95 |
| 4,456,510 | 6/1984 | Murakami et al. ............. 204/101 |
| 4,499,077 | 2/1985 | Stockel et al. ................ 514/635 |
| 4,557,925 | 12/1985 | Lindahl et al. ................ 424/19 |
| 4,568,517 | 2/1986 | Kaspar et al. ................ 252/188.2 |
| 4,614,549 | 9/1986 | Ogunbiyi et al. .............. 422/28 |
| 4,654,208 | 3/1987 | Stockel et al. ................ 514/635 |
| 4,689,215 | 8/1987 | Ratcliff . |
| 4,690,773 | 9/1987 | Ogunbiyi et al. ............ 252/174.12 |
| 4,767,559 | 8/1988 | Kruse et al. .................. 252/90 |
| 4,767,559 | 8/1988 | Kruse et al. .................. 252/90 |
| 4,855,135 | 8/1989 | Ratcliff ...................... 424/661 |
| 4,986,990 | 1/1991 | Davidson et al. ............ 424/665 |

FOREIGN PATENT DOCUMENTS

| | | |
|---|---|---|
| 0082798 | 6/1983 | European Pat. Off. . |
| 0147100 | 7/1985 | European Pat. Off. . |
| 0196075 | 1/1986 | European Pat. Off. . |
| 0209071 | 1/1987 | European Pat. Off. . |
| 0255041A1 | 5/1988 | European Pat. Off. . |
| 0278224 | 8/1988 | European Pat. Off. . |
| 3626082A1 | 11/1988 | Fed. Rep. of Germany . |
| 2139260A | 11/1984 | United Kingdom . |
| 2173017A | 10/1986 | United Kingdom . |
| 2151039A | 7/1988 | United Kingdom . |
| WO85/04107 | 9/1985 | PCT Int'l Appl. . |
| WO86/05695 | 10/1986 | PCT Int'l Appl. . |

OTHER PUBLICATIONS

Chemical Abstracts Selects: Issue 2, 1987.

*Primary Examiner*—R. Bruce Breneman
*Assistant Examiner*—Zeinab El-Arini
*Attorney, Agent, or Firm*—Gordon L. Peterson; Frank J. Uxa, Jr.

[57] ABSTRACT

A method for disinfecting a lens is disclosed. The method comprises contacting a lens to be disinfected in a liquid medium with at least one chlorine dioxide precursor in the presence of at least one acidic component effective to increase the rate of formation of chlorine dioxide from the chlorine dioxide precursor, thereby disinfecting the lens; and adjusting the acidity of the liquid medium containing the disinfected lens. Compositions useful in the above-noted method are also disclosed.

74 Claims, No Drawings

METHODS TO DISINFECT CONTACT LENSES

BACKGROUND OF THE INVENTION

This invention relates to disinfecting lenses, such as contact lenses In particular, the invention relates to methods and compositions useful to quickly and effectively disinfect lenses while reducing eye irritation caused by disinfecting the lenses.

Contact lenses should be periodically disinfected to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. In fact, the general rule has been that the amount of eye irritation to be expected is directly proportional to the rate of disinfecting. Fast-acting disinfectants, such as hydrogen peroxide, cause significant ocular irritation if placed directly in the eye. Thus, when using such disinfectants a thorough rinsing and/or neutralization step is required to remove substantially all traces of the disinfectant. Thus, in Gaglia, et al U.S. Pat. No. 3,912,451 a metal component is used to remove hydrogen peroxide from soft contact lenses which have been sterilized with hydrogen peroxide. Also, such disinfectants are often not stable and tend to lose their potency over time. A fast-acting, stable lens disinfecting system which is not as prone to cause eye irritation would clearly be advantageous.

It has been proposed to disinfect substrates using an acidic solution containing chlorites, such as sodium chlorite. Alliger U.S. Pat. No. 4,084,747 and International Patent Publication (PCT) No. W035/04107 are directed to such systems. The acidic conditions apparently cause liberation of chlorine dioxide, which acts as a disinfectant. Lenses, and in particular contact lenses, have not been disclosed as being disinfected in such acidic media. High acidity can cause substantial eye irritation.

In addition to disinfecting the contact lens, it should also be cleaned, e.g., of debris such as protein-based debris which accumulates on the lens during use. Such lens cleaning is often done in the presence of one or more enzymes. See, for example, Karageozian U.S. Pat. No. 3,910,296. In many instances, a complete lens maintenance procedure involves first enzymatic cleaning followed by the separate lens disinfecting step. One system in which lens cleaning and disinfecting occur substantially simultaneously is disclosed in Huth, et al U.S. Pat. Reissue No. 32,672. This system employs a solution to contact the lens which comprises a disinfecting amount of peroxide and an effective amount of peroxide-active proteolytic enzyme for a time sufficient to remove substantially all protein accretions and to disinfect the lens.

SUMMARY OF THE INVENTION

New compositions and methods for disinfecting lenses, e.g., contact lenses, have been discovered. These compositions and methods utilize the controlled formation of chlorine dioxide, a very effective contact lens disinfectant. The ability to control the formation of chlorine dioxide allows one to effectively and efficiently ship and store the chlorine dioxide precursor prior to use. Then, substantially on demand, the precursor is activated to provide the desired amount of chlorine dioxide. In addition, the present system provides for controlling the acidity of the medium in which the disinfected lens is present, thus reducing the risk of eye irritation caused by the disinfecting procedure.

An additional benefit of being able to control the formation or release of the disinfectant is that it allows one to sequentially clean the lens, e.g., using enzymatic cleaning, and disinfect the lens, preferably in one step. This is very convenient for the ultimate consumer, e.g., the contact lens wearer, and provides him/her with an easy and time effective way to maintain his/her lenses. The contact lens wearer experiences more comfort and less irritation because his/her contact lenses are more apt to be clean and disinfected.

In one broad aspect, the invention involves a method and composition for disinfecting a lens, e.g., a contact lens. A lens to be disinfected is contacted with a composition including a first liquid medium and at least one chlorine dioxide precursor. This contacting takes place in the presence of at least one acidic component in an amount to effect formation of chlorine dioxide from the precursor. This contacting results in the lens being disinfected. The disinfected lens is contacted with a second liquid medium having reduced acidity relative to the first liquid medium. The first and second liquid media may be derived from the same source, i.e., the same liquid medium. In this embodiment, after the lens is disinfected, the acidity of the liquid medium containing the disinfected lens is adjusted, e.g., reduced, for example, so that the pH of this liquid medium is within the physiological range for humans. Because the acidity is reduced, the disinfected lens may be placed directly into the wearer's eye. Alternately, a simple saline rinse of the disinfected lens may be employed before placing the lens back in the wearer's eye.

In another broad aspect of the invention, a composition, which is useful in performing the present method, is provided and comprises at least one acidic component and at least one acidity adjusting component, preferably at least one basic component and/or at least one buffer component. The acidic component or components selected are capable of increasing the acidity of a liquid medium into which the composition is released, e.g., a liquid medium containing a chlorine dioxide precursor, as described herein The acidity adjusting component or components are capable of reducing the acidity of a liquid medium, e.g., as described herein, into which such component or components are released. The composition is structured so that upon exposure to a liquid medium the acidity adjusting component or components are released after the acidic component or components are released This sequential release feature of these compositions provides for the acidity of the chlorine dioxide precursor-containing liquid medium to be increased to effect chlorine dioxide formation and disinfect the lens, and then for the acidity of the liquid medium to be reduced, e.g., to within the human physiological range, to reduce eye irritation.

The above-noted composition may further include at least one solid chlorine dioxide precursor, e.g., sodium chlorite, which is released, e.g., dissolved, in a liquid medium. The acidic component effects formation of disinfecting amounts of chlorine dioxide from the precursor upon release of the acidic component into the liquid medium. Alternately, a solid composition, e.g., in the form of an item such as tablet, pill or the like, can be provided which includes both at least one chlorine dioxide precursor and at least one acidic component which are present in amounts effective to produce lens disinfecting amounts of chlorine dioxide in a liquid medium.

In another broad aspect, the lens to be disinfected or the disinfected lens is contacted with at least one enzyme capable of removing debris from a contact lens in an amount effective to remove debris from the lens being contacted. This removal or cleaning step may be conducted before or after the disinfecting step. In one embodiment, the liquid medium which includes the chlorine dioxide precursor also includes the enzyme. The acidic component and/or the acidity adjusting component, e.g., a basic and/or buffer component, may be present during the enzyme cleaning, for example, in a substantially inactive, e.g., unreleased, form. If the enzyme, precursor and acidic component are all present during the enzyme cleaning, the acidic component should be present in a substantially inactive form. This will allow the cleaning to occur without interference from the presence of chlorine dioxide. For example, the acidic component and the acidity adjusting component may be present in a delayed release form, e.g., in a tablet, pill, or the like, together with the enzyme which is released first, e.g., substantially immediately on being exposed to the liquid medium. After sufficient time for effective enzymatic cleaning of the lens has elapsed, the active acidic component is released. This causes formation of chlorine dioxide and results in disinfecting the enzymatically cleaned lens. After a further period of time, the active acidity adjusting component is released to reduce the acidity of the liquid medium, e.g., to a pH within the human physiological range. Alternately, the enzyme can be present in a delayed release form together with the acidity adjusting component. In this embodiment, the enzyme is released after the lens is disinfected. Thus, the enzyme is released at substantially the same time or after the acidity adjusting component is released.

The present lens cleaning and disinfecting preferably take place in a single step. The lens wearer does not need to closely monitor the process or to intervene to adjust the acidity of the liquid medium, or to change solutions between the cleaning and disinfecting steps. Preferably, this acidity adjusting is done automatically, i.e., without human intervention. Overall, the present invention is very easy and effective to use. This encourages the lens wearer to disinfect, and preferably clean, his/her contact lenses frequently, resulting in more comfort and less eye irritation.

DETAILED DESCRIPTION OF THE INVENTION

The present system is applicable for disinfecting all types of lenses, e.g., contact lenses, which are benefited by periodical disinfecting. Such lenses, e.g., conventional hard contact lenses and soft contact lenses, may be made of any suitable material or combination of materials and may have any suitable configuration.

One important feature of the present invention is the use of chlorine dioxide precursors. Such precursors are adapted to provide for controlled formation of disinfecting amounts of chlorine dioxide. Thus, such precursors allow the disinfectant, e.g., chlorine dioxide, to be shipped and stored with minimum loss of disinfecting power. Chlorine dioxide is formed when needed and wanted, i.e., in a liquid medium contacting a lens to be disinfected. As used herein, a disinfecting amount of chlorine- dioxide means such amount as will reduce the microbial burden or load by one log order in 3 hours or less, preferably in 1 hour or less, more preferably in 10 minutes or less. Of course, the amount of chlorine dioxide employed should not cause any substantial damage to the lens being treated.

In general, the chlorine dioxide precursors useful in the present invention are those which form or produce chlorine dioxide in a liquid medium, preferably a liquid aqueous medium, in the presence of one or more of the presently useful acidic components. Thus, in mildly acidic conditions, in particular at a pH of less than about 6 and especially in the range of about 3 to about 5, the production of chlorine dioxide is effected. Among the preferred chlorine dioxide precursors useful in the present invention is stabilized chlorine dioxide. The term "stabilized chlorine dioxide" as used herein means one or more chlorine dioxide-containing complexes and/or one or more chlorite-containing components and/or one or more other entities capable of forming chlorine dioxide in a liquid medium in the presence of the presently useful acidic components.

Examples of such chlorite-containing components include metal, chlorites, and in particular alkali metal and alkaline earth metal chlorites. A specific example of a chlorite-containing component which is useful as a chlorine dioxide precursor is technical gradesodium chlorite. Among the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide complexes, is not completely understood. The manufacture or production of certain chlorine dioxide precursors is described in McNicholas U.S. Pat. No. 3,278,447, which is hereby incorporated in its entirety by reference herein. Specific examples of useful chlorine dioxide precursor sources include products such as that sold under the trademark Dura Klor by Rio Linda Chemical Company, Inc. and that sold under the trademark Anthium Dioxide by International Dioxide, Inc. An especially useful chlorine dioxide precursor source is a product sold under the trademark Purogene by Bio-Cide International, Inc. The chlorine dioxide precursor may be included in a liquid medium at a predetermined concentration, e.g., a concentration chosen to provide a disinfecting amount of chlorine dioxide- in the presence of the acidic component or components. Preferably, the liquid medium has sufficient chlorine dioxide precursor so as to have a potential of producing chlorine dioxide in the range of about 0.002% to about 3% (weight chlorine dioxide/volume of liquid medium).

In one embodiment, the chlorine dioxide precursor includes a functionality selected from carbonate, borate, sulfate, phosphate, and mixtures thereof.

Any suitable acidic component may be employed in the present invention. The primary criteria for such component is that it have the ability to increase the acidity of the liquid medium containing at least one chlorine dioxide precursor sufficiently to effect formation of chlorine dioxide from such chlorine dioxide precursor, and preferably sufficiently to effect formation of lens disinfecting amounts of chlorine dioxide from the presently useful chlorine dioxide precursors. Such acidic components should also have no substantial detrimental effect on the lens to be disinfected.

Examples of the presently useful acidic components include mineral acids, salts of such mineral acids, carboxylic acids, salts of such carboxylic acids and mixtures thereof. The mineral acids include, for example, nitric acid, sulfuric acid, hydrogen halides, phosphoric acid and the like. The carboxylic acids include both mono- and poly-, e.g., di-, tri- and the like, carboxylic acids, and preferably include 1 to about 10 carbon atoms per molecule. One or more nonhydrocarbonaceous groups, e.g., hydroxy groups, halide groups and the like, may be appended to the carboxylic acid. If an acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

In one embodiment of the present invention, a solid composition is provided which includes at least one chlorine dioxide precursor and at least one acidic component. This composition, in the form of a tablet, pill or the like, includes sufficient solid chlorine dioxide precursor and acidic component to produce a lens disinfecting amount of chlorine dioxide when released in a liquid medium. The above —noted chlorite—containing components are particularly useful as the solid chlorine dioxide precursor.

The liquid medium or media, e.g., first and second liquid media, used are selected to have no substantial detrimental effect on the lens being treated and to allow and even facilitate the present lens treatment or treatments. The liquid media are preferably aqueous-based. A particularly useful liquid aqueous medium is that derived from saline, e.g., a conventional saline solution. During the disinfecting contacting, it is preferred that the liquid aqueous medium have a pH of about 6 or less, in particular in the range of about 3 to about 5.

After the disinfecting contacting, the disinfected lens is contacted with a liquid medium having reduced acidity relative to the liquid medium in the disinfecting contacting. For example, the disinfected lens can be contacted with e.g., rinsed and/or soaked in, a second liquid medium, e.g., a conventional saline or buffered saline solution, separate and apart from the liquid medium, the first liquid medium, used in the disinfecting contacting. The second liquid medium has reduced acidity relative to the liquid medium used in the disinfecting contacting. Alternately, the acidity of the liquid medium used in the disinfecting contacting can be reduced in an acidity adjusting step, as described herein. In any event, after the acidity is reduced, the disinfected lens is preferably present in a liquid aqueous medium which preferably has a pH in the range of about 6.5 to about 8, and more preferably about 7.5. Such pH ranges are substantially consistent with the normal physiological pH for humans. Thus, after disinfecting and acidity reduction, the disinfected lens may be placed directly in the eye. Alternately, a simple saline rinse of the disinfected lens may be employed before placing the lens in the eye. This is in contrast to other systems which require elaborate neutralization procedures before the lens is suitable for placement in the eye.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

The present acidity adjusting step preferably provides for reducing the acidity of the liquid medium containing the disinfected lens. Thus, if the liquid medium is aqueous-based, the adjusting step preferably provides for increasing the pH of the disinfected lens-containing liquid medium. In one embodiment, an acidity adjusting component useful to reduce the acidity of the liquid medium is introduced into the liquid medium after the lens has been disinfected. However, this acidity adjusting component may be introduced into the liquid medium at substantially the same time as is the acidic component introduced into the liquid medium. As is discussed hereinafter, the acidity adjusting component can be included in a delayed release form, e.g., tablet, pill or the like, designed to release the acidity adjusting component into the liquid medium after the pill or tablet is exposed to the liquid medium. For example, the acidity adjusting component can be included in a composition with the acidic component with the composition structured to release the acidity adjusting component into a liquid medium after the acidic component is released into the liquid medium.

The acidity adjusting component is preferably selected from the group consisting of basic components, buffer components and mixtures thereof. The acidity adjusting component may be a mixture of at least one basic component and at least one buffer component. The acidity adjusting component should have no substantial detrimental effect on the lens being treated. Examples of the presently useful acidity adjusting components include borates, dibasic phosphates, carbonates, bicarbonates, mixtures thereof and the like. The acidity adjusting components preferably are compounds including alkali metals or alkaline earth metals, in particular alkali metals, especially sodium.

The amount of the acidity adjusting component or components employed is sufficient to achieve the desired acidity reduction in the liquid medium containing the disinfected lens.

In one embodiment, a composition is provided which includes at least one enzyme and at least one acidic component capable of increasing the acidity of a liquid medium into which the acidic component is released. The composition is structured so that upon introduction into a liquid medium, the enzyme is released before the acidic component is released. The acidic component may be as described elsewhere herein.

The enzyme or enzymes used are capable of removing debris from a contact lens. Among the types of debris that form on contact lens during normal use are protein-based debris, mucin-based debris, lipid-based debris and carbohydrate-based debris. One or more types of debris may be present on a single contact lens. The amount of such enzyme or enzymes used (included in the present compositions), if any, is effective to remove substantially all of at least one type of debris from a debris laden contact lens in a reasonable time, preferably in the range of about 1 minute to about 12 hours. The active enzyme-containing liquid medium preferably contains sufficient enzyme to provide between about 0.001 to about 5 Anson units of activity, more preferably between about 0.01 to about 1 Anson units of activity, per single lens treatment.

The enzyme employed may be selected from enzymes which are conventionally employed in the enzymatic cleaning of contact lenses. For example, many of the enzymes disclosed in Huth et. al. Reissue U.S. Pat. No. 32,672 are useful in the present invention. This patent is incorporated in its entirety by reference herein. Among the useful enzymes are those selected from proteolytic enzymes, lipases and mixtures thereof. The enzyme may be one or more carbohydrate-active enzymes. Specific examples of useful enzymes include proteases, amylases, lipases and mixtures thereof.

Using the composition structured to release the enzyme before the acidic component allows the cleaning action of the enzyme to occur prior to or before the production of chlorine dioxide for lens disinfecting. It is advantageous to have a reduced concentration of, preferably substantially no, chlorine dioxide present during the enzymatic lens cleaning. This is so because the chlorine dioxide may deactivate or even destroy (oxidize) the enzyme.

The cleaning action may take place after the lens disinfecting. In one embodiment, a composition is provided which includes at least one enzyme and at least one acidity adjusting component, as described elsewhere herein. This composition is structured so that upon introduction into a liquid medium the enzyme is released at substantially the same time or after the acidity adjusting component is released. Reducing the acidity of the liquid medium reduces chlorine dioxide production from the chlorine dioxide precursor in the liquid medium. This allows an effective amount of enzyme to be present in the liquid medium to clean the lens, e.g., the disinfected lens. This composition preferably includes a reducing agent effective to chemically reduce chlorine dioxide in a liquid medium. The reducing agent is preferably released into the liquid medium at substantially the same time the acidity adjusting component is released. This released reducing agent acts to chemically reduce chlorine dioxide present in the liquid medium. More preferably, the reducing agent acts to chemically reduce substantially all the chlorine dioxide present in the liquid medium. With the chlorine dioxide chemically reduced, and thus inactivated, the enzyme is able to perform its cleaning function with little or no interference from residual chlorine dioxide.

The use of a chlorine dioxide reducing agent has more general applicability in the present invention. One possible source of eye irritation from the disinfected lens is residual chlorine dioxide. Thus, a reducing agent effective to chemically reduce chlorine dioxide may be advantageously used after the disinfecting contacting of the present invention in order to reduce the concentration of residual chlorine dioxide.

Any suitable chlorine dioxide reducing agent may be used in the present invention, provided that it functions as described herein and has no substantial detrimental effect on the lens being treated and on the human wearing the treated lens. A particularly useful example of such a reducing agent is N-acetylcysteine. The amount of the reducing agent used is such to chemically reduce the desired amount of chlorine dioxide. In one embodiment, the amount of reducing agent employed is about 50% to about 150% that amount needed to chemically reduce all the chlorine dioxide present in the liquid medium when the reducing agent is released into the liquid medium. The amount of reducing agent used may be at least that amount needed to chemically reduce all the chlorine dioxide present in the liquid medium when the reducing agent is released into the liquid medium.

In another embodiment, the acidic component is included in the composition in a substantially inactive form and/or is released on a delayed release basis. For example, the enzyme, acidic component and acidity adjusting component may be present together in a single item, i.e., a layered tablet, pill or the like. After the item is introduced with the liquid medium containing the chlorine dioxide precursor, the enzyme first becomes available to remove debris from the to-be-cleaned lens. At this time, i.e., when the enzyme is cleaning the lens, the acidic component and the component remain in the item, effectively out of contact with the chlorine dioxide precursor. After a period of time, e.g., a predetermined period of time for which the item is designed, the acidic component is released into the liquid medium. This causes chlorine dioxide formation which, in turn, results in disinfecting the lens in the liquid medium. After a second period of time, the acidity adjusting component is released into the liquid medium containing the disinfected lens to reduce the acidity of this liquid medium, as described elsewhere herein.

Tablets, pills or the like which release their ingredients in a sequential, time delayed manner are well known and can be produced using conventional technology. Therefore, a detailed description of such items and such production technology is not presented here. However, such tablets, pills or the like are preferably designed to allow one component sufficient time to perform its function before releasing another component which may interfere with the functioning of the first component. For example, if the item contains both an enzyme and an acidic component, the item is preferably designed to allow the enzyme sufficient time to remove at least a major amount, and more preferably substantially all, of at least one type of debris, in particular the protein-based debris, from the lens in the liquid medium. In other words, such items are preferably designed so that sufficient time elapses between release of the enzyme and release of the acidic component to allow the enzyme to perform its cleaning function. Such sufficient time is preferably in the range of about one minute to about 2 hours, more preferably about five minutes to about one hour.

Whether or not the enzyme is present in the composition (delayed release item), the composition is preferably designed to allow the acidic component to be released before the acidity adjusting component. The interval between the time the acidic component is released and the time the acidity adjusting component is released is preferably sufficient to provide for the chlorine dioxide which is formed after release of the acidic component to disinfect the lens. This interval is preferably in the range of about 1 minute to about 12 hours, more preferably about 0.2 to about 4 hours.

The following examples illustrate certain aspects of the present invention.

EXAMPLE 1

Two (2) aqueous solutions were prepared containing the same concentration of a stabilized chlorine dioxide product, sold by Bio-Cide International, Inc. under the trademark Purogene. One solution had a pH of 6.5 and the other solution had a pH of 6.0. Each of these solutions was monitored for chlorine dioxide concentration with time.

Results of these tests were as follows:

| Time, Minutes | pH = 6.0 ClO$_2$ Concentration, ppm., by wt. | pH = 6.5 ClO$_2$ Concentration, ppm., by wt. |
| --- | --- | --- |
| 0 | 0.944 | 0.023 |
| 30 | 0.601 | 0.094 |
| 90 | 0.338 | 0.039 |
| 120 | 0.318 | 0.258 |

These results indicate that increased acidity (reduced pH) has a beneficial effect on the rapid production of chlorine dioxide from chlorine dioxide precursors. Thus, it is advantageous, e.g., to provide for faster lens disinfecting, to contact the lens to be disinfected with a chlorine dioxide precursor in an aqueous liquid medium at a pH lower than the human physiological range. This treatment may involve a substantial neutralization step in order to ready the disinfected lens for wear. However, the overall effect may be beneficial, e.g., in that a reduced overall amount of time is required for effective lens disinfecting.

EXAMPLE 2

A solution containing deionized water, 0.85% (w/v) of sodium chloride, 0.10% (w/v) of boric acid, and 50 ppm. w/v of the stabilized chlorine dioxide product identified in Example 1 was prepared. Each of the concentrations of stabilized chlorine dioxide product set forth in the Examples of this application is stated in terms of potential chlorine dioxide. One portion of this solution was buffered to a pH of 7.9, while the other portion was buffered to a pH of 6.8. Varying amounts of tartaric acid were added to different samples of each of these portions. The samples were then tested, following the standard procedure, to determine the D-value with respect to various microorganisms. The D-value is defined as the length of time required to reduce the microbial burden or load by one log unit.

Results of these test were as follows:

| Microorganism | Extrapolated D-value at 23° C., min. | | | | |
| --- | --- | --- | --- | --- | --- |
| pH = 6.8 | | | | | |
| Tartaric Acid, ppm. | 30 | 40 | 50 | 60 | 70 |
| Free Chlorine Dioxide, ppm. | 10.74 | 17.08 | 37.94 | 25.38 | 32.47 |
| S. marcescens | <.84 | <.84 | <.84 | <.84 | <.84 |
| S. aureus | <.87 | <.87 | <.87 | <.87 | <.87 |
| P. aeruginosa | <.85 | <.85 | <.85 | <.85 | <.85 |
| A. fumigatus | <.83 | <.83 | <.83 | <.83 | <.83 |
| pH = 7.9 | | | | | |
| Tartaric Acid, ppm. | 30 | 40 | 50 | 60 | 70 |
| Free Chloride Dioxide, ppm. | 0.03 | 0.11 | 0.05 | 0.15 | 0.23 |
| S. marcescens | 5.13 | <.85 | 2.56 | <.85 | 2.56 |
| S. aureus | 10.17 | 2.54 | 2.54 | 12.24 | 2.54 |
| P. aeruginosa | 19.48 | <.87 | 2.6 | <.87 | <.87 |
| A. fumigatus | 109 | 109 | 150 | 162.2 | 70.6 |

These results of Examples 1 and 2 indicate that chlorine dioxide per se can be present in a sufficient amount in a liquid medium to be effective to disinfect contact lenses. Thus, these results demonstrate that sufficient chlorine dioxide can be provided in a liquid medium, particularly at a reduced pH, to reduce the microbial burden or load by one log order in a period of time generally deemed acceptable for disinfecting contact lenses.

EXAMPLE 3

A lens disinfecting system was provided which included a solution, an activator tablet and a neutralizer tablet.

The solution was purified water with the following components: 0.85% (w/v) sodium chloride; 0.10% (w/v) boric acid; and 0.005% (w/v) the stabilized chlorine dioxide product identified in Example 1. The pH of this solution is about 7.7 to 7.9.

The activator tablet had the following composition: 27.0 mg. tartaric acid; 10.0 mg. anhydrous sodium carbonate; 40.6 mg. sugar-based binder/filler; and 2.4 mg. polyethylene glycol (molecular weight of about 3350) (a conventional tabletting lubricant).

The neutralizer tablet had the following composition: 3.0 mg. tartaric acid; 21.0 mg. sodium carbonate; 23.3 mg. sugar-based binder/filler; 1.5 mg. polyethylene glycol (molecular weight of about 3350); and 1.2 mg. N-acetylcysteine.

The activator tablet was placed in 10 ml. of the solution and the resulting material was monitored for pH and chlorine dioxide concentration. Chlorine dioxide appeared in 28±3 seconds. The pH of the material was noted at 3.6±0.1. After 5 minutes, the chlorine dioxide concentration was 43.62±0.38 ppm. After 30 minutes, the chlorine dioxide concentration was 41.12±0.92 ppm.

The neutralizer tablet was then placed in the material. The neutralizer tablet dissolved in the material. Upon shaking the material, the characteristic color of chlorine dioxide which was present disappeared immediately. The pH of the final solution was 6.61±0.03 and drifted up to about 7 after 30 minutes. The chlorine dioxide concentration of the final solution is 0.16±0.04 ppm.

The amount of chlorine dioxide produced by combining the activator tablet with the solution is effective to kill most microorganisms in about 10 minutes or less, e.g., about 1 to 2 minutes. Disinfection of soft contact lens can be accomplished in about 1 to 2 minutes. However, at this point, the solution has a disagreeable odor and color, a low pH and may contain sufficient chlorine dioxide to cause eye irritation.

The neutralizer tablet is added to the solution to raise the pH to a comfortable level and consume chlorine dioxide. A disinfected contact lens could be taken from the neutralized system and placed directly in the eye without irritation or discomfort.

EXAMPLE 4

Three (3) solutions were prepared by combining varying amounts of tartaric acid with the solution identified in Example 3. The solutions were then tested, following the standard procedure, to determine the D-value with respect to various microorganisms.

Results of these tests were as follows:

| Microorganisms | Solution 1 pH = 4.62 ClO$_2$ Conc. = 37.94 ppm. | Solution 2 pH = 4.17 ClO$_2$ Conc. = 39.14 ppm. | Solution 3 pH = 3.97 ClO$_2$ Conc. = 43.13 ppm. |
| --- | --- | --- | --- |
| | Extrapolated D-value at 23° C., min. | | |
| S. marcescens | <0.84 | | |
| S. aureus | <0.87 | | |
| P. aeruginosa | <0.85 | | |
| A. fumigatus | <0.83 | 0.88 | <2.63 |
| S. epidermidis | | <0.87 | |
| C. albicans | | 0.83 | |

-continued

|  | Solution 1<br>pH = 4.62<br>ClO$_2$ Conc. =<br>37.94 ppm. | Solution 2<br>pH = 4.17<br>ClO$_2$ Conc. =<br>39.14 ppm. | Solution 3<br>pH = 3.97<br>ClO$_2$ Conc. =<br>43.13 ppm. |
|---|---|---|---|
| Micro-<br>organisms | Extrapolated D-value at 23° C., min. | | |
| A. niger |  |  | <2.63 |

These D-values are sufficiently short so that a contact lens needs to soak in a solution containing 45 ppm. chlorine dioxide for about 10 minutes or less, e.g., about 2 to about 5 minutes, to provide acceptable lens disinfecting.

EXAMPLE 5

A lens disinfecting system was provided which included the solution as identified in Example 3, the activator tablet identified in Example 3, and a coated neutralizer tablet. This coated neutralizer tablet had the following composition: 15.0 mg. tartaric acid; 30.0 mg. anhydrous sodium carbonate; 28.5 mg. sugar-based binder/filler; 3.5 mg. polyethylene glycol (molecular weight of about 3350); 3.0 mg. N-acetylcysteine; and 12.0 mg. a conventional delayed or sustained release coating (sold by Colorcon under the trademark Opadry).

Both the activator tablet and the coated neutralizer tablet were placed in 10 ml. of the solution at the same time. The following observations were made. Chlorine dioxide was first detected 31±5 seconds after the tablets were introduced, with the maximum chlorine dioxide concentration occurring at 1 to 1.5 minutes after tablet introduction. The activator tablet dissolved completely in 151±11 seconds, while the coated neutralizer tablet started to dissolve after 118±3 seconds and started to effervesce after 146±5 seconds. The coated neutralizer tablet dissolved completely in 397±7 seconds. The final pH of the solution was 6.73±0.13 and the final chlorine dioxide concentration was 0.01±0.02 ppm.

The time during which an effective concentration of chlorine dioxide is present in the solution is sufficiently long to disinfect a soft contact lens. Moreover, the final pH and final chlorine dioxide concentration are such that the disinfected lens can be placed in the eye without undue discomfort or irritation.

EXAMPLE 6

A lens disinfecting system was provided which included the solution as identified in Example 3, and a bilayer tablet which weighed 44 mg. One layer, the activator layer, of the bilayer tablet contained 65% by weight tartaric acid; 24.09% by weight anhydrous sodium carbonate; 6.91% by weight a conventional sugar—or sucrose—based bulking agent; and 4% by weight polyethylene glycol (molecular weight of about 3350). The other layer, the neutralizer layer, of the bilayer tablet contained 54.29% by weight anhydrous sodium carbonate; 3% by weight N-acetylcysteine; 26.71% by weight a conventional sugar—or sucrose—based bulking agent; 8% by weight polyethylene glycol (molecular weight of about 8000); 8% by weight hydroxy propyl methyl cellulose (100 centipoise 2% by wt. aqueous solution at 20° C.). The activator layer dissolved faster than the neutralizer layer.

The relative proportions of activator layer and neutralizer layer were such that when the bilayer tablet was introduced into 10 ml. of the solution the following was observed. The pH of the solution dropped to 3.8 in 80 seconds after the bilayer tablet was introduced. The activator layer was completely dissolved after one (1) minute. The neutralizer layer was slow to dissolve. Chlorine dioxide appeared after 140 seconds and the level of chlorine dioxide remained constant (as did the pH of the solution) until after 8 minutes when the solution was stirred. Upon stirring, the characteristic chlorine dioxide color immediately disappeared and the pH of the solution changed to 8.35. About 10 to 20% of the bilayer tablet remained undissolved after 8 minutes.

These observations indicate that a bilayer tablet can be structured to effectively disinfect a contact lens, and then return the pH of the solution to the physiological range and reduce the chlorine dioxide concentration of the solution.

EXAMPLE 7

A lens disinfecting system is provided which includes the solution as identified in Example 3 and a core-type tablet. This core-type tablet is like a tablet within a tablet. The outer shell is the activator and the inner core is the neutralizer. The activator shell has the following composition: 27 mg. tartaric acid; 10 mg. anhydrous sodium carbonate; 60 mg. a conventional sugar—or sucrose—based bulking agent; and 3 mg. polyethylene glycol (molecular weight of about 3350). The neutralizer core has the following composition: 5 mg. tartaric acid; 35 mg. anhydrous sodium carbonate; 3 mg. N-acetylcysteine; 15.2 mg. sugar-based binder/filler and 1.8 mg. polyethylene glycol (molecular weight of about 3350).

When this core-type tablet is introduced into 10 ml. of the solution, the activator shell rapidly dissolves and the pH is lowered to 3 to 4. Chlorine dioxide is generated. After the entire activator shell has dissolved, e.g., in about 2 to 5 minutes, the neutralizer core dissolves so that in another additional 2 to 3 minutes substantially all of the chlorine dioxide i removed from the solution and the pH is raised to a comfortable level of about 6.5 to 7.9.

In much the same way as the system of Example 5, the present disinfecting system is effective to disinfect a soft contact lens.

EXAMPLE 8

A lens disinfecting system is provided which is the same as that in Example 7 except for the composition of the neutralizer core.

In the present system, the neutralizer core has the following composition: 8.2 mg. tartaric acid; 57.8 mg. anhydrous sodium carbonate; 4.5 mg. N-acetylcysteine; 2.4 mg. polyethylene glycol (molecular weight of about 3350); 6.39 mg. sugar-based binder/filler; and 0.71 mg. Subtilisin A (an enzyme conventionally used to clean contact lenses).

This system functions in much the same manner as the system of Example 7 except that the Subtilisin A is released with the other components of the neutralizer core. Thus, after the pH of the solution is raised to about 6.5 to 7.9, enzymatic cleaning of the lens in the solution begins. The enzyme can be inactivated by chlorine dioxide. However, the chlorine dioxide is removed from the solution sufficiently rapidly so that the enzyme remains effective to clean the lens.

EXAMPLE 9

A lens disinfecting system is provided which includes the solution identified in Example 3 and a pouch having two separate types of particles or spheres. The activator particles have the same composition as the activator tablet of Example 3 and the neutralizer particles have the same composition as the neutralizer tablet of Example 3, except that none of the particles have any sugar-based binder/filler or polyethylene glycol. In addition, the activator particles are coated, e.g., with an appropriate coating polymer, only to ensure their integrity. The neutralizer particles are coated so that they release their components about 5 to 7 minutes after the particles are introduced into the solutions.

The lens to be disinfected is placed in 10 ml. of the solution. The contents of the pouch is emptied into the solution. This system provides a chlorine dioxide concentration pattern and solution pH pattern with time similar to corresponding patterns described in Example 5. The lens is removed from the solution effectively disinfected and ready for use.

EXAMPLE 10

A lens disinfecting system was provided which included a buffered saline solution, an activator tablet, a saline rinse and a saline soak.

The buffered saline solution was purified water with the following components: 0.85% (w/v) sodium chloride; and 0.10% (w/v) boric acid.

The activator tablet had the following composition: 16.8 mg. tartaric acid; 5.6 mg. anhydrous sodium carbonate; 55.0 mg. sugar-based binder/filler; 2.4 mg. polyethylene glycol (molecular weight of about 3350); and 0.22 mg. technical grade sodium chlorite.

The activator tablet was placed in 10 ml. of the buffered saline solution. The pH of the solution was reduced to 3.63±0.24. Chlorine dioxide appeared in about one (1) minute and the chlorine dioxide concentration of the solution ten minutes after the tablet was placed in the solution was 6.46±2.63 ppm.

A contact lens is placed in 10 ml. of the buffered saline solution. An activator tablet is also placed in the solution. After about 30 minutes, the lens is removed, and rinsed thoroughly with the buffered saline solution. Finally, the lens is soaked in 10 ml. of the buffered saline solution for 30 minutes. The lens is effectively disinfected and ready for immediate use, i.e., in the eye of a human being.

EXAMPLE 11

Five (5) solutions were prepared by combining the buffered saline solution identified in Example 10 with varying amounts of technical grade sodium chlorite and tartaric acid. The solutions were then tested, following the standard procedure, to determine the D-value with respect to various microorganisms.

Results of these tests were as follows:

| Micro-organism | Extrapolated D-value at 23° C., min. | | |
| --- | --- | --- | --- |
| | Solution 1<br>pH = 3.81<br>ClO$_2$ Conc. =<br>4.61 ppm. | Solution 2<br>pH = 3.84<br>ClO$_2$ Conc. =<br>4.54 ppm. | Solution 3<br>pH = 3.86<br>ClO$_2$ Conc. =<br>4.39 ppm. |
| C. albicans | 0.5 | | |
| A. niger | 10.1 | | |
| S. marcescans | | | 0.17 |
| S. aureus | | | 0.17 |
| | Solution 4<br>pH = 3.86<br>ClO$_2$ Conc. =<br>6.32 ppm. | Solution 5<br>pH = 3.89<br>ClO$_2$ Conc. =<br>8.99 ppm. | |
| A. fumigatus | 0.5 | | |
| C. albicans | | 0.5 | |
| A. niger | | 4.3 | |

These D-values demonstrate that reduced concentrations, e.g. in the range of about 4 to about 10 ppm., of chlorine dioxide may be effective to disinfect a contact lens provided that a sufficient soak time, e.g., on the order of about 1 minute to about 1 hour, is allowed for the disinfecting to take place.

EXAMPLE 12

A lens disinfecting system was provided which included the solution as identified in Example 10 and an activator/neutralizer tablet. This tablet had the following composition: 16.8 mg. tartaric acid; 5.6 mg. anhydrous sodium carbonate; 38.18 mg. sugar-based binder/filler; 2.4 mg. polyethylene glycol (molecular weight of about 3350); 0.11 mg. technical grade sodium chlorite; and 16.91 mg. coated anhydrous sodium carbonate. This anhydrous sodium carbonate was coated, using a conventional coating composition, in such a way so that the release of the sodium carbonate was delayed for a time after the tablet was introduced into the solution. When the activator/neutralizer tablet was introduced into 10 ml. of the solution, the following was observed. The solution contained about 4.5 ppm. chlorine dioxide within 10 minutes. The pH at this point was about 6.0. A lower pH may have occurred before the 10 minute period.

After lens disinfecting with this system, the disinfected lens may be rinsed with and/or soaked in the buffered saline solution prior to the application of the lens to the eye. This rinsing and/or soaking adjusts the pH to within the comfortable human physiological range.

EXAMPLE 13

A lens disinfecting system is provided which is the same as that identified in Example 12 except that the activator/neutralizer tablet further includes an effective amount of coated N-acetylcysteine. This coated N-acetylcysteine is coated in such a way to release the N-acetylcysteine at substantially the same time the coated anhydrous sodium carbonate is released.

When this activator/neutralizer tablet is introduced into 10 ml. of the solution substantially the same observations are made as were made in Example 12. In addition, substantially all of the residual chlorine dioxide in the solution is consumed after about four (4) hours. Thus, using this system substantially no active chlorine dioxide is present on the disinfected contact lens when it is placed in the eye.

EXAMPLE 14

This example illustrates a lens cleaning/disinfecting embodiment of the present invention.

A protein-based debris laden contact lens is placed in a plastic container. A quantity, i.e., 10 ml., of the solution identified in Example 3 is added to the container. The pH of this solution is about 7.5.

A layered, delayed release tablet is dropped into the solution in the container. The center core of this tablet contains sodium carbonate. In intermediate layer of this tablet contains citric acid. The outer layer of the tablet includes a quantity of a proteolytic enzyme. The tablet is structured to release the enzyme into the solution immediately upon introducing the tablet into the solution.

Further, this tablet is structured to release the citric acid about 30 minutes after the tablet is introduced into the solution; and to release the sodium carbonate about 2 hours after the tablet is introduced into the solution. The tablet is sized so that sufficient enzyme is present to remove substantially all of the protein-based debris from the protein-based debris laden lens; sufficient citric acid is present to reduce the pH of the solution in the container to about 4 when the citric acid is released; and sufficient sodium carbonate is present to increase the pH of the acidified solution in the container to about 7.5 when the sodium carbonate is released.

Upon being dropped into the solution, the enzyme in the outer layer of the tablet is released and begins to attack and remove the protein-based debris on the lens. In 30 minutes, substantially all of the protein-based debris is removed from the lens, and the citric acid is introduced to the solution and the pH falls to about 4. A lens disinfecting amount of chlorine dioxide is produced from the chlorine dioxide precursor in the solution. This chlorine dioxide acts to disinfect the cleaned lens. Two hours after the tablet is introduced into the solution, the sodium carbonate is released. This results in an increase in the pH of the solution in the container to a value of about 7.5, within the physiological range for humans.

Ten and one half-hours after the tablet is dropped into the solution, the cleaned and disinfected lens is removed from the solution. After a buffered saline rinse the lens is ready to be placed in the lens wearer's eye.

This cleaning/disinfecting procedure requires only one step as opposed to conventional separate cleaning and disinfecting steps with the need for human intervention between the steps. Thus, the present system is very convenient to use and reduces the amount of time the contact lens wearer must actively spend to clean and disinfect his/her lenses. In addition, because the pH of the solution and lens is in the physiological range at the end of the procedure, there is reduced risk of eye irritation as the result of incomplete rinsing. In short, the present system provides very effectively and efficiently for cleaned and disinfected contact lenses which can be worn with a reduced risk of eye irritation.

If it is desired to disinfect the contact lens without enzymatic cleaning, the enzyme containing layer of the tablet can be eliminated. In this embodiment, the tablet is structured to release the citric acid substantially immediately after the tablet is introduced into the solution. However, as before, the final pH of the solution is about 7.5 and, therefore, the disinfected contact lens can be worn with a reduced risk of eye irritation.

EXAMPLE 15

Example 14 is repeated except that technical grade sodium chlorite is used as the chlorine dioxide precursor. This technical grade sodium chlorite has the following composition:
80% by weight $NaClO_2$
13% by weight $NaCl$
5% by weight $Na_2CO_3$
2% by weight $NaClO_3$ The combined cleaning/disinfecting treatment, and the disinfecting embodiment in which no enzyme is present, provide effectively treated contact lens, i.e., a cleaned and disinfected contact lens or a disinfected contact lens, as the case may be, which can be worn with a reduced risk of eye irritation.

While this invention has been described with respect to various specific examples and embodiments, it is to be understood that the invention is not limited thereto and that it can be variously practiced within the scope of the following claims.

What is claimed is:

1. A method for disinfecting a contact lens which comprises:
    contacting a contact lens in a first liquid medium with a chlorine dioxide precursor in the presence of an acidic component in an amount to effect formation of a disinfecting amount of chlorine dioxide from said chlorine dioxide precursor, thereby disinfecting said contact lens;
    introducing an acidity adjusting component into said first liquid medium, said acidity adjusting component being effective to adjust and control said first liquid medium containing said disinfected contact lens at reduced acidity after being released into said first liquid medium; and
    contacting said disinfected contact lens with a second liquid medium having reduced acidity relative to said first liquid medium used in said contact lens contacting.

2. The method of claim 1 wherein each of said first and second liquid media is an aqueous liquid medium.

3. The method of claim 2 wherein said contacting with said first liquid medium occurs at a pH of about 6 or less.

4. The method of claim 3 wherein said second liquid medium has a pH in the range of about 6.5 to about 8.

5. The method of claim 3 wherein said second liquid medium has a pH of about 7.5.

6. The method of claim 2 wherein said contactings occur at a temperature in the range of about 0° C. to about 100° C.

7. The method of claim 2 wherein said contacting in said first liquid medium occurs for a time in the range of about 1 minute to about 12 hours.

8. The method of claim 1 wherein said first liquid medium and said second liquid medium are derived from the same liquid medium.

9. The method of claim 1 wherein said chlorine dioxide precursor is introduced into said first liquid medium as a solid.

10. The method of claim 1 wherein said contacting with said second liquid medium includes at least one of rinsing said disinfected contact lens in a saline solution and soaking said disinfected contact lens in a saline solution.

11. The method of claim 10 wherein said saline solution includes a buffering agent.

12. The method of claim 1 wherein said chlorine dioxide precursor is stabilized chlorine dioxide.

13. The method of claim 1 wherein said chlorine dioxide precursor is selected from the group consisting of chlorine dioxide-containing complexes and mixtures thereof.

14. The method of claim 1 wherein said chlorine dioxide precursor is selected from the group consisting of complexes of chlorine dioxide and carbonate, complexes of chlorine dioxide and bicarbonate, and mixtures thereof.

15. The method of claim 1 wherein said chlorine dioxide precursor is selected from the group consisting of chlorite-containing components and mixtures thereof.

16. The method of claim 1 wherein said chlorine dioxide precursor includes a functionality selected from the group consisting of carbonate, borate, sulfate, phosphate, and mixtures thereof.

17. The method of claim 1 which further comprises introducing an acidic component into said first liquid medium.

18. The method of claim 17 wherein said acidic component is introduced into said first liquid medium as a solid.

19. The method of claim 18 wherein said chlorine dioxide percursor is introduced into said first liquid medium as a solid.

20. The method of claim 19 wherein said chlorine dioxide precursor and said acidic component are introduced into said first liquid medium at substantially the same time.

21. The method of claim 1 wherein said acidic component is selected from the group consisting of mineral acids, carboxylic acids, acidic salts and mixtures thereof.

22. The method of claim 1 wherein said acidic component is selected from the group consisting of carboxylic acids and mixtures thereof.

23. The method of claim 1 wherein said acidic component is selected from the group consisting of alkali metal hydrogen phosphates, citric acid, lactic acid, tartaric acid and mixtures thereof.

24. The method of claim 1 wherein said acidic component is introduced into said first liquid medium in the form of a pill or tablet.

25. The method of claim 1 wherein said acidity adjusting component is introduced into said first liquid medium as a solid.

26. The method of claim 1 wherein said acidity adjusting component is selected from the group consisting of basic components, buffer components and mixtures thereof.

27. The method of claim 1 wherein said acidity adjusting component comprises a mixture of at least one basic component and at least one buffer component.

28. The method of claim 1 wherein said acidic component is introduced into said first liquid medium prior to said acidity adjusting component being introduced into said first liquid medium.

29. The method of claim 1 wherein said acidic component and said acidity adjusting component are introduced into said first liquid medium at substantially the same time.

30. The method of claim 29 wherein said acidic component and said acidity adjusting component are each a part of the same item which is introduced into said first liquid medium.

31. The method of claim 30 wherein said item is structured to release said acidic component prior to releasing said acidity adjusting component.

32. The method of claim 31 wherein said item is structured to release said acidity adjusting component after being introduced into said first liquid medium a sufficient time to provide for the contact lens to be disinfected.

33. The method of claim 1 wherein said second liquid medium includes a reducing agent in an amount effective to chemically reduce at least a portion of the chlorine dioxide formed from said chlorine dioxide precursor.

34. The method of claim 1 which further comprises introducing a reducing agent effective to chemically reduce at least a portion of the chlorine dioxide formed from said chlorine dioxide precursor into said first liquid medium.

35. The method of claim 34 wherein said acidity adjusting agent and said reducing agent are introduced into said first liquid medium at substantially the same time.

36. The method of claim 1 which further comprises contacting the contact lens in a liquid medium with at least one enzyme capable of removing debris from a contact lens in an amount effective to remove debris from the contact lens.

37. The method of claim 36 wherein the contact lens is contacted with said at least one enzyme prior to said contacting with said chlorine dioxide precursor.

38. The method of claim 37 wherein said liquid medium is said first liquid medium.

39. The method of claim 38 wherein said at least one enzyme and said acidic component are introduced into said first liquid medium at substantially the same time.

40. The method of claim 39 wherein said at least one enzyme and said acidic component are each part of the same item introduced into said first liquid medium.

41. The method of claim 40 wherein said item is structured to release said at least one enzyme prior to releasing said acidic component.

42. The method of claim 38 wherein the contact lens is contacted with said at least one enzyme after being disinfected.

43. The method of claim 42 wherein said liquid medium is said first liquid medium.

44. The method of claim 43 which further comprises introducing a reducing agent effective to chemically reduce at least a portion of the chlorine dioxide formed from said chlorine dioxide precursor into said first liquid medium.

45. The method of claim 36 wherein said at least one enzyme is selected from the group consisting of proteolytic enzymes, lipases and mixtures thereof.

46. The method of claim 36 wherein said at least one enzyme is selected from the group consisting of carbohydrate active enzymes and mixtures thereof.

47. The method of claim 36 wherein said at least one enzyme is selected from the group consisting of proteases, amylases, lipases and mixtures thereof.

48. The method of claim 38 wherein said at least one enzyme and said acidity adjusting component are introduced into said first liquid medium at substantially the same time.

49. The method of claim 48 wherein said at least one enzyme and said acidity adjusting component are each part of the same item introduced into said first liquid medium.

50. The method of claim 49 wherein said same item is structured to release said acidity adjusting component prior to releasing said at least one enzyme or at substantially the same time as said at least one enzyme is released.

51. The method of claim 49 wherein said same item further includes a reducing agent effective to chemically reduce at least a portion of the chlorine dioxide formed from said chlorine dioxide precursor.

52. The method of claim 51 wherein said same item is structured to release said acidity adjusting component and said reducing agent prior to releasing said at least one enzyme or at substantially the same time as said at least one enzyme is released.

53. A method for disinfecting a contact lens which comprises:
(1) contacting a contact lens in a first liquid medium with a chlorine dioxide precursor in the presence of an acidic component in an amount to effect formation of a disinfecting amount of chlorine dioxide from said chlorine dioxide precursor, thereby disinfecting said contact lens; and
(2) contacting said disinfected contact lens in a second liquid medium derived from said first liquid medium and having an acidity at the conclusion of step (2) which is reduced relative to said first liquid medium used in step (1).

54. The method of claim 53 wherein each of said first and second liquid media in an aqueous liquid medium.

55. The method of claim 54 wherein said contacting with said first liquid medium occurs at a pH of about 6 or less, and said second liquid medium has a pH in the range of about 6.5 to about 8.

56. The method of claim 53 wherein said chlorine dioxide precursor is introduced into said first liquid medium as a solid.

57. The method of claim 53 wherein said chlorine dioxide precursor is stabilized chlorine dioxide.

58. The method of claim 53 which further comprises introducing said acidic component into said first liquid medium.

59. The method of claim 53 wherein said acidic component is selected from the group consisting of mineral acids, carboxylic acids, acidic salts and mixtures thereof.

60. The method of claim 53 wherein said second liquid medium includes a reducing aent in an amount effective to chemically reduce at least a portion of the clorine dioxide formed from said chlorine dioxide precursor.

61. The method of claim 53 which further comprises introducing a reducing agent effective to chemically reduce at least a portion of the chlorine dioxide formed from said chlorine dioxide precursor into said first liquid medium.

62. The method of claim 53 which further comprises contacting the contact lens in a liquid medium with at least one enzyme capable of removing debris from a contact lens in an amount effective to remove debris from the contact lens.

63. The method of claim 62 wherein the contact lens is contacted with said at least one enzyme prior to step (1).

64. The method of claim 63 wherein said liquid medium is said first liquid medium, 65. The method of claim 64 wherein said enzyme and said at least one acidic component are introduced into said first liquid medium at substantially the same time.

66. The method of claim 62 which further comprises introducing an acidity adjusting component into said first liquid medium.

67. The method of claim 66 wherein said at least one enzyme and said acidity adjusting component are introduced into said first liquid medium at substantially the same time.

68. The method of claim 67 wherein said at least one enzyme and said acidity adjusting component are each part of the same item introduced into said first liquid medium.

69. The method of claim 68 wherein said same item is structured to release said acidity adjusting component prior to releasing said at least one enzyme is released.

70. A method for disinfecting a contact lens which comprises:
(1) contacting a contact lens in a first liquid medium with a chlorine dioxide precursor in the presence of an acidic component in an amount to effect formation of a disinfecting amount of chlorine dioxide from said chlorine dioxide precursor, thereby disinfecting said contact lens; and
(2) contacting said disinfected contact lens with a second liquid medium having an acidity at the conclusion of step (2) which is reduced relative to said first liquid medium used in step (1), said second liquid medium including at least one reducing agent in an amount effective to chemically reduce at least a portion of the chlorine dioxide formed from said chlorine dioxide precursor.

71. The method of claim 70 wherein each of said first and second liquid media is an aqueous liquid medium.

72. The method of claim 71 wherein said contacting with said first liquid medium occurs at a pH of about 6 or less, and said second liquid medium has a pH in the range of about 6.5 to about 8.

73. The method of claim 70 wherein said chlorine dioxide precursor is stabilized chlorine dioxide.

74. The method of claim 70 which further comprises introducing said reducing agent into said first liquid medium.

* * * * *

UNITED STATES PATENT AND TRADEMARK OFFICE
CERTIFICATE OF CORRECTION

PATENT NO. : 5,279,673
DATED : January 18, 1994
INVENTOR(S) : Dziabo et al

It is certified that error appears in the above-indentified patent and that said Letters Patent is hereby corrected as shown below:

Column 18, line 35, claim 42; delete "38" and insert
   --36--.

Column 18, line 54, claim 48; delete "38" and insert
   --36--.

Column 20, line 24, claim 69; after "enzyme" insert
   --or at substantially the same time as said at least
   one enzyme--.

Signed and Sealed this

Twenty-third Day of May, 1995

Attest:

Attesting Officer

BRUCE LEHMAN

Commissioner of Patents and Trademarks